United States Patent
Chin et al.

[11] Patent Number: 5,897,557
[45] Date of Patent: Apr. 27, 1999

[54] BONE FRACTURE REINFORCEMENT STRUCTURE AND METHOD

[76] Inventors: Albert K. Chin, 2021 Newell Rd., Palo Alto, Calif. 94303; Lawrence S. Levin, 3800 Westchester Rd., Durham, N.C. 27707

[21] Appl. No.: 09/042,077

[22] Filed: Mar. 13, 1998

[51] Int. Cl.$^6$ .................................................. A61B 17/56
[52] U.S. Cl. ............................................. 606/71; 606/69
[58] Field of Search ................................. 606/71, 69, 65, 606/70, 73, 72

[56] References Cited

U.S. PATENT DOCUMENTS

| | | | |
|---|---|---|---|
| 4,388,921 | 6/1983 | Sutter et al. ............................... | 606/71 |
| 5,665,089 | 9/1997 | Dall et al. .................................. | 606/70 |
| 5,672,177 | 9/1997 | Seldin ....................................... | 606/71 |
| 5,827,286 | 10/1998 | Incavo et al. ............................. | 606/71 |

*Primary Examiner*—Michael Buiz
*Assistant Examiner*—Kevin Truong
*Attorney, Agent, or Firm*—Fenwick & West, LLP

[57] ABSTRACT

Apparatus and method for reducing a fractured long bone includes a cannula having a transparent tapered tip for facilitating visualization of the cannula being advanced along the bone from an initial incision remote from the fracture. The cannula includes a selectively inflatable balloon near the tip to expand a working cavity adjacent the bone. An arched, elongated positioning fixture is inserted into the working cavity with lower edges including facing grooves therein disposed against the bone. A support gate is slid into position across the fracture along the groove in the fixture, and holes in the support plate are referenced by the fixture from above the overlying skin. Small incisions are formed with reference to holes in the support plate for insertion of bone screws through the incisions and the fixture to secure the support plate to the bone across the fracture under visualization of an endoscope positioned within the arched space of the fixture. The fixture is then removed from the working cavity slidably along the secured support plate, and the incisions are then closed.

7 Claims, 7 Drawing Sheets

BONE FRACTURE REINFORCEMENT STRUCTURE AND METHOD

RELATED APPLICATION

The subject matter of this application relates to the subject matter set forth in application Ser. No 08/907,691, entitled "Tissue Separation Cannula With Dissection Probe and Method," filed on Aug. 18, 1997, by Albert K. Chin.

FIELD OF THE INVENTION

This invention relates to bone reinforcements, and more particularly to alignment structures and method for attaching reinforcement plates to fractured long bones.

BACKGROUND OF THE INVENTION

Conventional surgical practices for attaching a supporting plate to a fractured long bone commonly requires forming a long skin incision to isolate and expose the fractured bone. Next, the fracture is reduced and fixed in the correct anatomical position, and the supporting plate is secured to the bone across the fracture with bone screws. One disadvantage of this conventional practice is extensive trauma attributable to the long surgical incision that contributes to the pain and the time required to heal both the fracture and the incised tissue overlying the bone.

Other conventional surgical practices require a small incision through which a fracture-supporting plate may be tunneled along the external surface of the bone into proper location across the fracture. Bone screws may then be placed percutaneously by inserting a sharp pin through the skin to locate holes in the plate to guide the drilling of pilot holes into the bone. Bone screws are then tightened into the pilot holes to secure the supporting plate to the bone at a position that can be visualized via fluoroscopy. One disadvantage of this practice is the accuracy of screw placement because two-dimensional visualization via fluoroscopy allows incorrect placement and skewing of the screws.

SUMMARY OF THE INVENTION

In accordance with one embodiment of the present invention, a tapered-tip balloon catheter is used to form an elongated cavity along the fractured bone from an initial incision under visualization through the tapered transparent tip using an endoscope disposed within the cannula to provide a field of view through the tip. The balloon may be relatively inelastic for selective inflation and deflation to assist in dissecting connective tissue from the fractured bone as the cannula is advanced therealong to form a working cavity adjacent the fractured bone. A positioning fixture is then inserted into the working cavity along the bone under visualization through an endoscope, and a support plate carried by the positioning fixture may be properly placed on the fractured bone and secured in position while being visualized through the endoscope located within the positioning fixture. Lower longitudinal edges of the positioning fixture are conveniently disposed along borders of the fractured bone to substantially center the positioning fixture and the support plate carried thereby on the fractured bone prior to securing the support plate to the bone. Thereafter, the positioning fixture may be removed from the working cavity by sliding the fixture along the secured plate and out through the initial incision. A removable drill guide selectively attaches to the positioning fixture above the skin to align a pilot-hole drill from above the skin with mating holes in the support plate within the working cavity.

DETAILED DESCRIPTION OF THE INVENTION

Figure 1A:
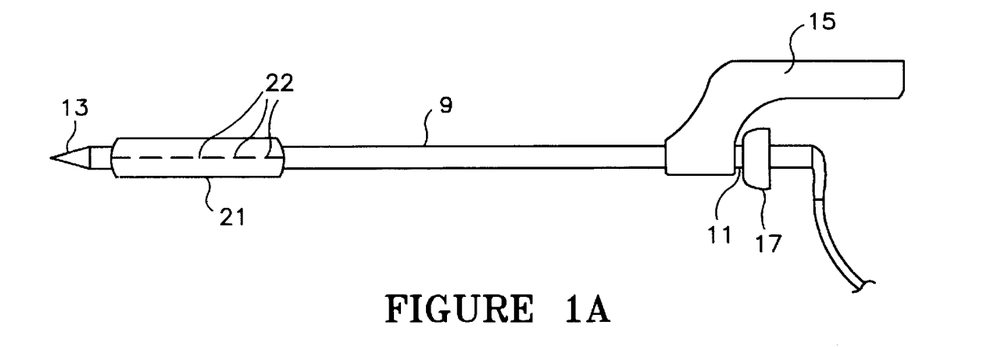
FIGS. 1A and 1B are side views of the balloon cannula according to one embodiment of the invention containing an endoscope therein, with a transparent tapered tip disposed over the remote end and with a handle and video camera disposed on the endoscope at the proximal end.

Referring now to FIG. 1A, there is shown an elongated cannula 9 including multiple lumina therein and having a remote end that is covered by a substantially rigid, transparent tapered tip 13. The proximal end of the cannula 9 is disposed within a handle 15, and supports a viewing end of an endoscope 11 having a conventional video camera 17 attached thereto for televising the field of view of the endoscope 11 through the transparent tip 13. The endoscope 11 extends along a lumen 8 within the cannula 9, as shown in FIG. 1C, from distal end adjacent the tapered tip 13 to the proximal end near the handle 15. A substantially inelastic, flexible balloon 19 is disposed about the cannula 9 near the remote end thereof within a perforated sheath 21, and is connected via a lumen 10 within the cannula 9, as shown in FIG. 1C, to a source of pressurized fluid (e.g., a manually-actuatable syringe within the handle 15) to control selective pressurization for inflating and deflating the balloon 19. The inelastic balloon 19 may be contained within a sheath 21 that is perforated 22 in lineal pattern to facilitate rupture and release of the collapsed or deflated balloon 19 upon initial pressurization and expansion of the balloon 19. The balloon may have a large inflated diameter of approximately 6–10 cm and a length of approximately 10 cm to form an elongated working cavity along the fractured bone. Manipulation of the cannula 9 along the bone may proceed under continuous visualization through the transparent tip 13, as later described herein.

Figure 1B:
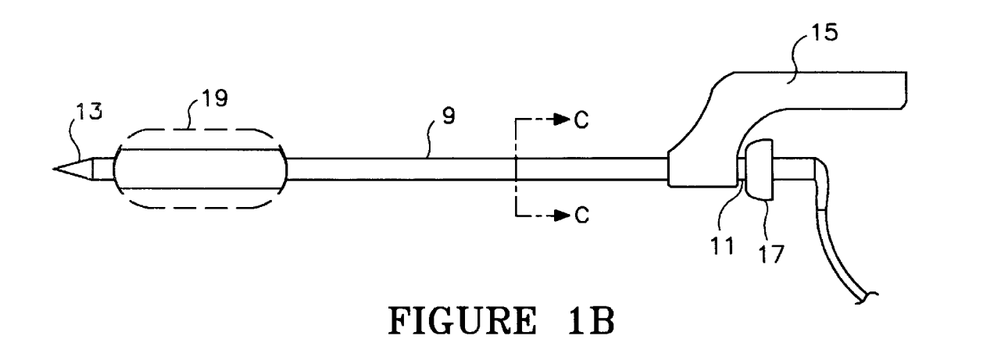
Figure 1C:
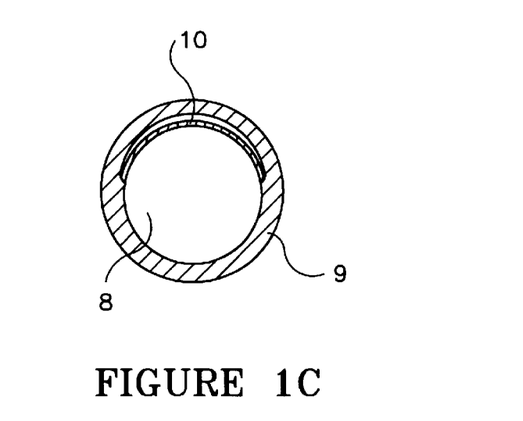
FIG. 1C is a sectional view of the cannula of FIGS. 1A and 1B showing multiple lumina therein.
Figure 2:
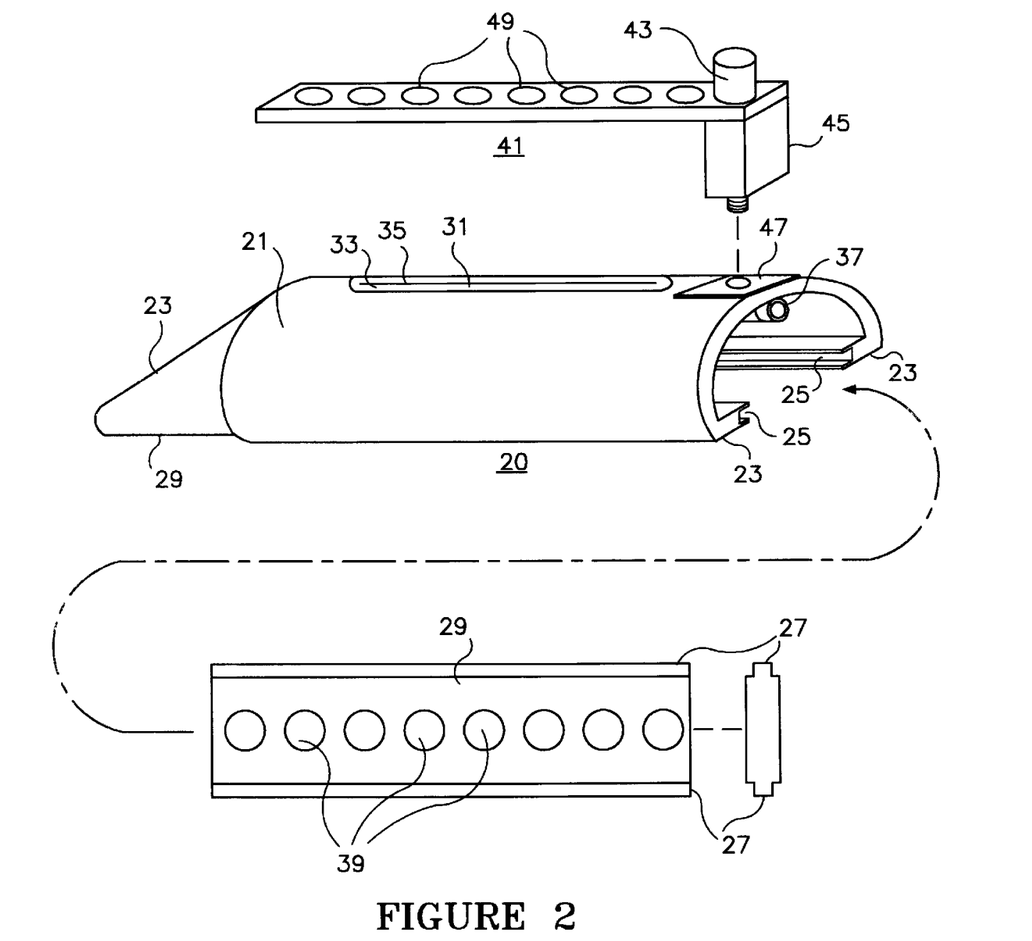
FIG. 2 is an exploded perspective view of the positioning fixture and support plate according to the present invention.

Referring now to the perspective view of FIG. 2, there is shown a positioning fixture 20 according to one embodiment of the present invention for temporary orientation along the fractured bone within the working cavity formed using the cannula of FIGS. 1A and 1B. The positioning fixture 20 includes a substantially semi-cylindrical or otherwise generally arched, rigid body 21 of about 30 cm length and about 5 cm diameter, with a semiconical or otherwise tapered tip 23 affixed to the distal end of the body 21. The body 21 includes a pair of rails or grooved extensions 23 disposed along the lower edges with guiding grooves 25 formed in facing relationship within the rails or extensions 23. These grooves 25 accommodate mating tongues 27 on a support plate 29 formed to slide within the grooves 25, as later discussed herein. Of course, tapered side edges of the support plate 29 may also be accommodated in facing V-shaped grooves along the lower edges. The tapered tip 23 has a base or lower edge 29 that is disposed above the level of the rails 23 to accommodate a support plate 29 sliding freely below the tip 23, as discussed later herein.

Figure 3:
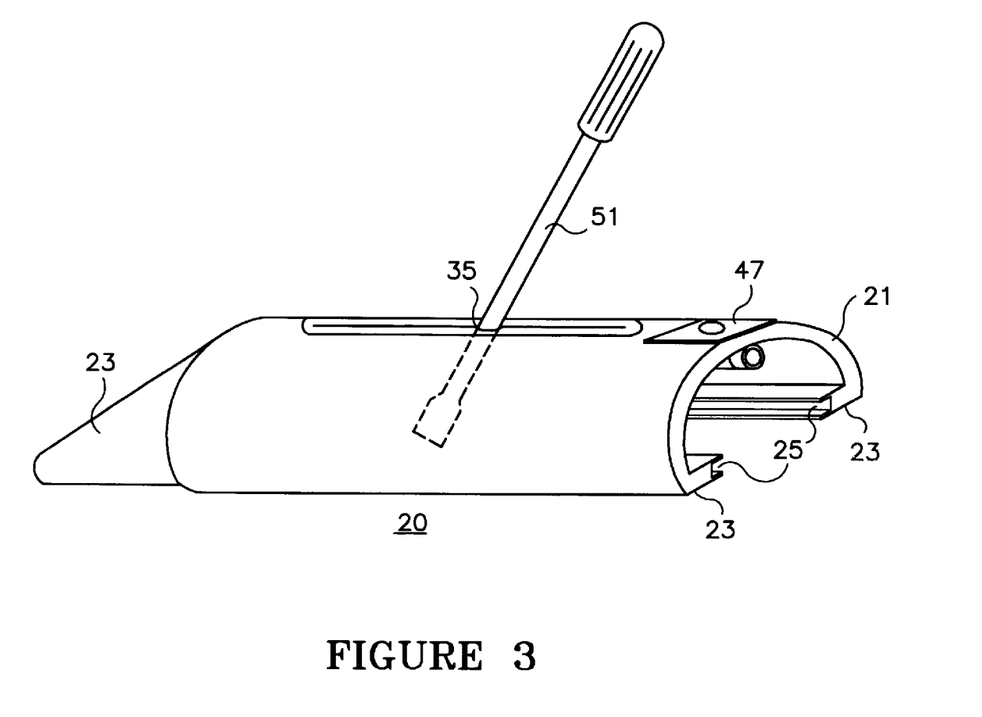
FIG. 3 is a perspective view of the positioning fixture illustrating a fastening tool disposed through a flexible elongated port in the upper region of the positioning fixture.

The semicylindrical body 21 includes an elongated window 31 in the top region of the body, and includes in the window 31 a flexible membrane 33 having an elongated slit 35 therein through which instruments may be inserted, as shown in FIG. 3 and as discussed later therein. A short length of hollow tubing 37 is disposed within the interior of the semi-cylindrical body 21 near the proximal end to serve as a holder for an endoscope that can be inserted into the interior of the body 21 to provide direct visualization of a fractured bone, a support plate 29 being positioned thereon, and bone screws being inserted through holes 39 in a support plate 29 into a fractured bone. The body 21 may be formed of transparent biologically-inert plastic to promote visualization of tissue surrounding the body using an endoscope positioned within the body.

A drill guide 41 is detachably mounted to the top of the body 21 near the proximal end thereof using threaded fastener 43 that passes through a spacer block 45 for mating threaded engagement with a reference block 47 on the body 21. The drill guide 41 includes holes 49 that align with holes 39 in a support plate 29 with such plate positioned along the grooves 25 at a reference location. Thus, the drill guide 41 may be selectively attached to the body 21 following proper positioning thereof on a fractured bone in preparation for drilling pilot holes at locations aligned with holes 39 in a support plate 29. Fastening tools 51, drills, bone screws, and the like, may be inserted through the slit 35 in the flexible membrane 33, as illustrated in FIG. 3, as required during installation of the support plate 29 on a fractured bone, as discussed later herein. The slit 35 in flexible membrane 33 thus remains normally closed adequately to keep fatty tissue and fluids from passing through the window 31 into the interior of body 21 potentially to interfere with endoscopic visualization of the fractured bone and installation of a supporting plate 29.

Figure 4A:
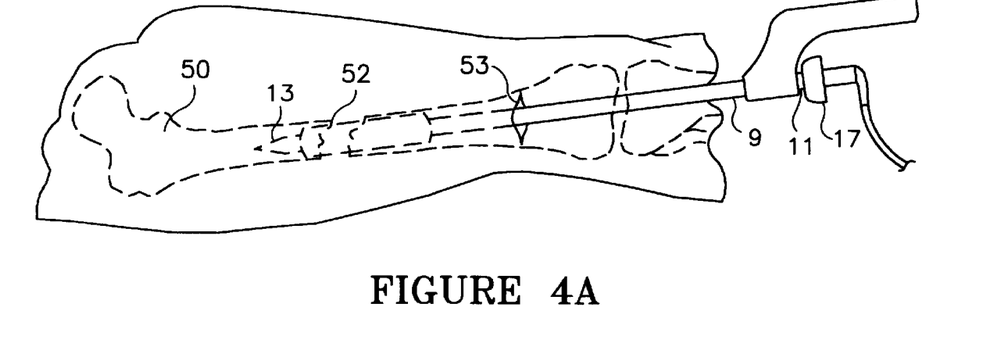
FIGS. 4A, 4B, and 4C are partial side views of a limb illustrating progressive stages of formation of a working cavity adjacent a fractured bone.
Figure 4B:
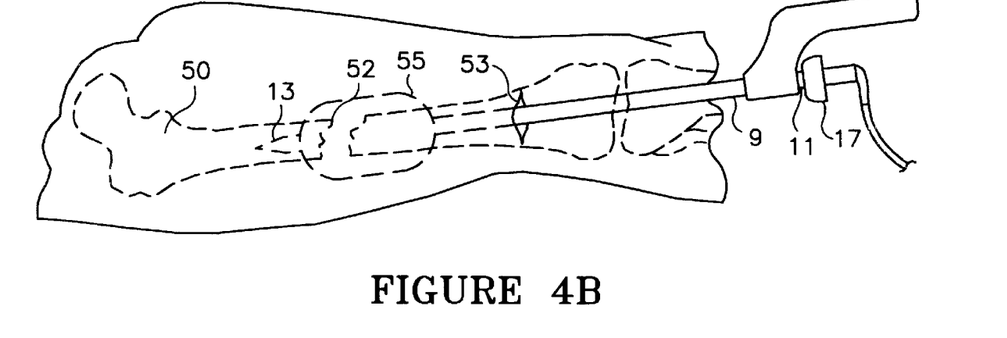
Figure 4C:
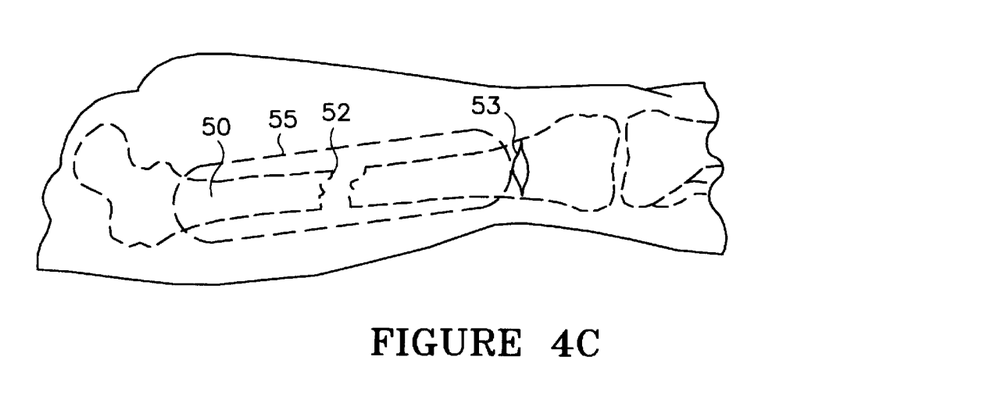

In operation to reduce fracture of a long bone 50, as illustrated in FIGS. 4A–C, a small incision 53 is first made remote from the fracture 52 to expose the fascia overlying the bone 50, and the cannula 9, as illustrated in FIG. 1A, is introduced into the incision 53. The cannula 9 is progressively advanced along the bone 50 and past the fracture 52, with visualization thereof through the transparent tapered tip 13 via the endoscope 11 and video camera 17. The balloon 19, confined within a perforated sheath 21, is then pressurized to rupture the sheath 21 along the perforations and expand surrounding tissue away from the fascia overlying the bone 50, thereby to form a working cavity 55 of about 10 cm diameter adjacent the fracture 52. The working cavity 54 may be expanded in length beyond the fracture 52, and between the fracture 52 and incision 53, as shown in FIG. 4C, to provide adequate working space adjacent the bone 50 and fracture 52 for placement of the positioning fixture and support plate.

Figure 5A:
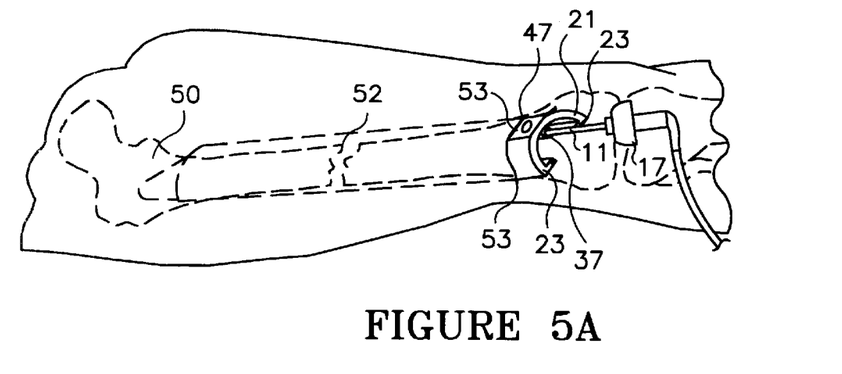
FIGS. 5A, 5B and 5C are partial side views of a limb illustrating manipulation of the positioning fixture, support plate, and drill guide according to the present invention.
Figure 5B:
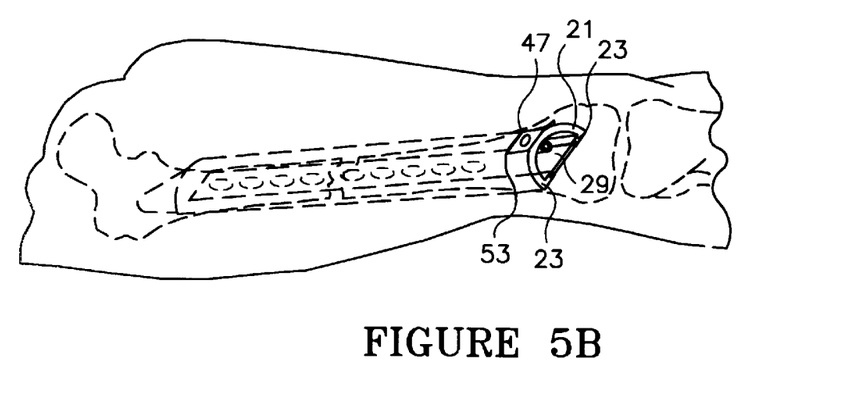
Figure 5C:
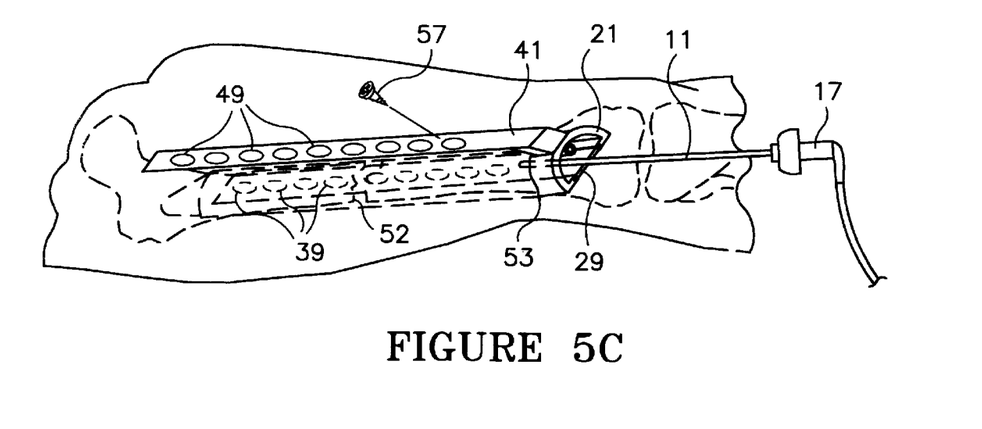

Referring now to FIGS. 5A–C, the positioning fixture 20 is shown inserted through incision 53 into the working cavity 55 adjacent the bone 50. The proximal end of the body 21 including the reference block 47 is shown protruding from the incision 53, with the rails 23 aligned substantially along, and straddling firmly upon, the bone 50. The fixture 20 is compressed against the bone 50 by the weight and elasticity of the overlying skin, thus helping to fix the bone segments in a reduced state in proper anatomical alignment. Visualization of placement of the fixture 20 in relation to the bone 50 and the fracture 52 is facilitated by endoscope 11 and video camera 17 that are supported by tubing 37 and that may be selectively positioned in the hollow space within the semi cylindrical body 21 in the position of straddling the bone 50.

Figure 6:
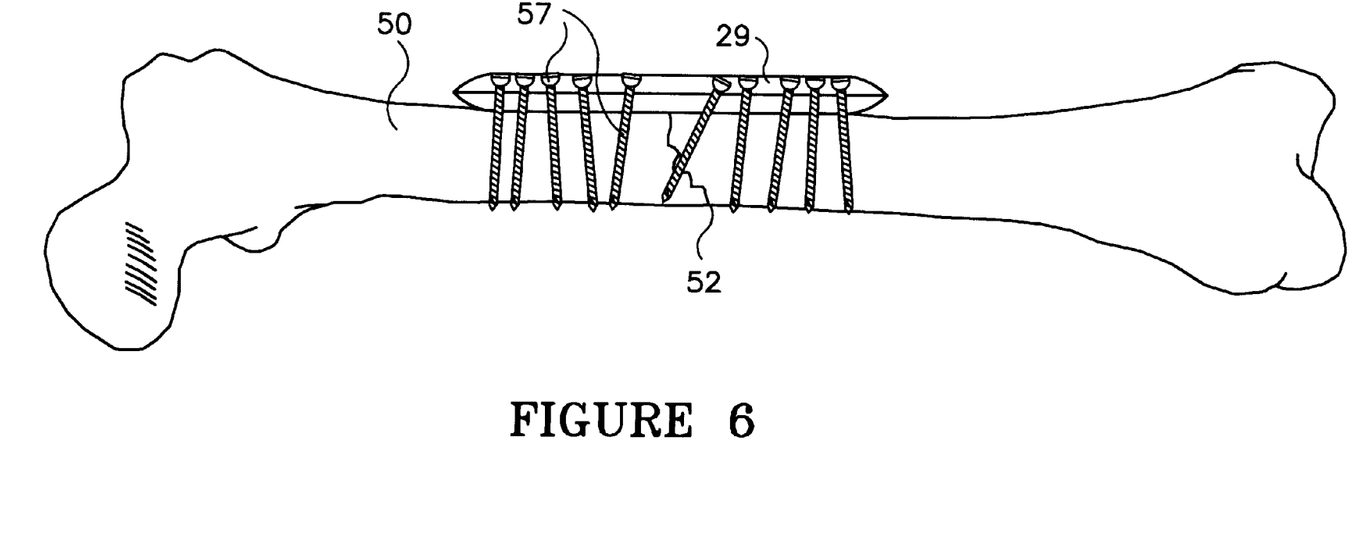
FIG. 6 is a pictorial view of a fractured bone with the support plate secured thereto via bone screws.

With the positioning fixture 20 properly placed, a support plate 29 may then be inserted along rails 23 into proper position overlaying the fracture 52, as shown in FIG. 5B, and the drill guide 41 may then be attached to the reference block 47 on the protruding proximal end of the body 21, as shown in FIG. 5C. The drill guide 41 thus installed on the reference block 47 of body 21 aligns drill guide holes 49 with holes 39 in support plate 29 with the support plate 29 referenced, for example, flush with the proximal end of body 21. Pilot holes may be drilled into the bone 50 using the holes 49 in drill guide as the directional guide for locating small incisions formed in the overlying skin, and for piercing through the slit 35 in the membrane 33 in the top region of the body 21, and for passing a drill through the holes 39 in support plate 29 into the segments of bone 50. Proper placement and angulation of pilot drill and of bone screws 57 that are subsequently installed can all be facilitated by placement of endoscope 11 (with the associated video camera 17) within the interior space within the body 21. Once the bone screws 57 firmly secure the support plate 29 to the bone 50, the positioning fixture 20 may be removed by sliding the body 21 along the support plate 29, through the incision 53 through which the positioning fixture 20 was initially was inserted, and the skin incisions may then be closed in conventional manner, leaving the fractured bone segments supported by support plate 29 and associated bone screws 57, as shown in FIG. 6.

Figure 7:
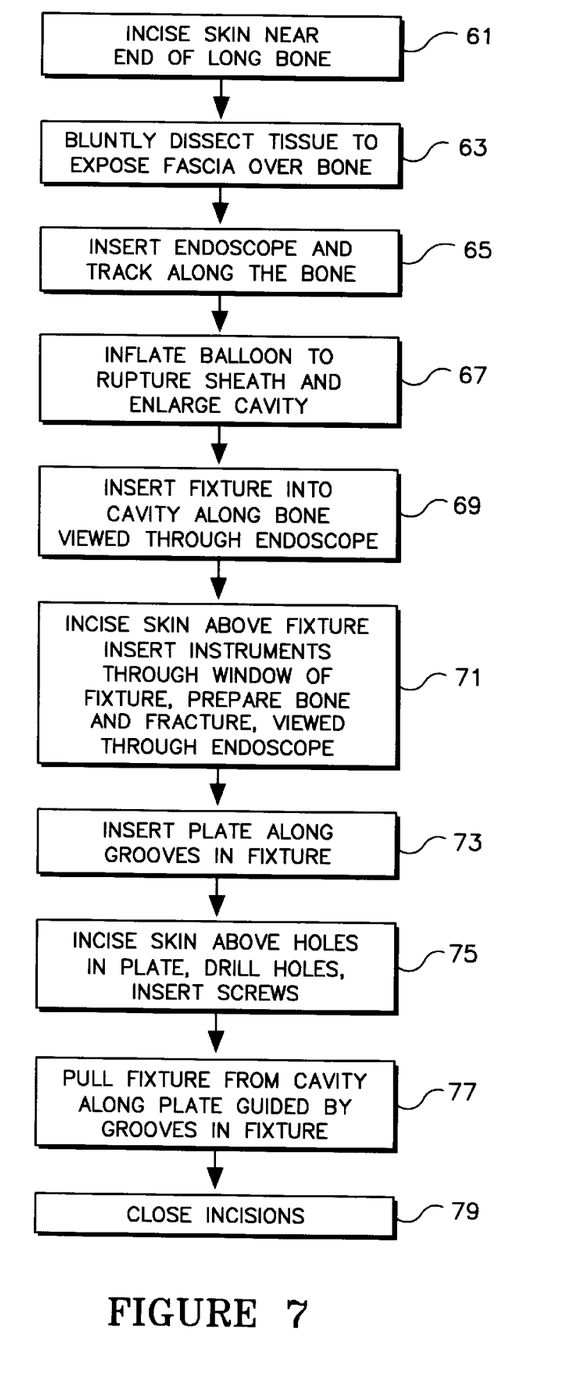
FIG. 7 is a flow chart illustrating the surgical procedure according to the present invention.

Referring now to the flow chart of FIG. 7, the procedure for reducing a fracture in a long bone according to the present invention proceeds from an initial incision formed 61 near one end of the bone away from the fracture. Blunt tissue dissection through the incision exposes 63 the fascia overlying the bone, and a balloon cannula having a tapered transparent tip, for example as illustrated and described with reference to FIGS. 1A and 1B, is advanced along the length of the bone 65 past the fracture to form a working cavity adjacent the bone under visualization from within and through the transparent tip 13. The balloon is inflated 67 to rupture the perforated confining sheath, and to expand the dimensions of the working cavity adjacent the bone. The sheath may be captivated on the cannula to assure removal with the cannula from within the working cavity.

The semi-cylindrical positioning fixture with a tapered tip on the remote end is then inserted 69 through the incision, into the working cavity, along the fractured bone, past the fracture, with a reference block left exposed near the proximal end of the body that protrudes from the incision. Small skin incisions may be made in alignment with the top of the body, and through the slit in the membrane along the top of the body to clear tissue and realign the bone segments at the fracture 71 under endoscopic visualization from within the space in the interior of the semi-cylindrical body.

A support plate may then be inserted 73 along grooves in the body of the positioning fixture to proper position adjacent the bone and traversing the fracture. A drill guide with a plurality of spaced holes is then attached to the protruding reference block on the body 21 to indicate alignment and location of corresponding holes in the support plate positioned within the grooves in the body, and small skin incisions may be made 75 at locations aligned with the holes in the drill guide. Pilot holes may be formed in the bone segments using a drill aligned through the drill guide, through incisions in the skin, through the slit in the membrane at the top of the body, and through corresponding holes in the support plate, and bone screws are then inserted and tightened to secure the support plate to the bone segments across the fracture. The semi-cylindrical body is then withdrawn from within the working cavity 77 along the secured support plate, and is removed through the initial skin incision. All incisions are then closed 79 in conventional manner.

Therefore, the apparatus and method of the present invention facilitates reduction of fractures in long bones through small incisions by bluntly dissecting a working cavity adjacent the bone segments for insertion therein of a positioning fixture for a supporting plate. The fixture may be positioned and the fracture may be cleaned and otherwise prepared for attachment of a supporting plate across the fracture under endoscopic visualization through and within the fixture. Small skin incisions in alignment with holes in the support plate facilitate insertion of bone screws to secure the support plate. The fixture may then be slidably withdrawn from the working cavity along mating grooves and rails in the fixture and support plate, leaving only small skin incisions and minor additional trauma surrounding the fracture for more rapid healing.

What is claimed is:

1. Surgical apparatus for selectively positioning a support plate adjacent a fractured bone, the apparatus comprising:

an elongated, substantially rigid body of arched cross-sectional shape having a distal end and a proximal end, and including spaced lower edges and an upper region of the arched body, the lower edges including guiding grooves therein substantially along the lengths of the lower edges between the distal and proximal ends of the body for slidably receiving a support plate therein;

a tapered tip attached at the distal end of the body; and an elongated window in the upper region of the body extending a selected dimension between the distal and proximal ends of the body in substantial alignment with the guiding grooves in the lower edges.

2. Surgical apparatus as in claim 1 further including a penetrable membrane disposed in said window to permit passage therethrough of selected objects having cross section smaller than dimensions of the window.

3. Surgical apparatus according to claim 2 wherein the membrane includes a length of flexible material including an elongated slit therein along a portion of the selected dimension of the window.

4. Surgical apparatus according to claim 1 including an elongated guide for selective attachment to the body, the body including a portion thereof near the proximal end for selective attachment thereto of the guide in substantial alignment with the elongated body.

5. Surgical apparatus according to claim 4 further including a support plate having a plurality of holes therethrough, in which the guide includes a plurality of holes therethrough in substantial alignment with corresponding holes in the support plate.

6. Surgical apparatus according to claim 1 wherein the tapered tip includes a lower edge disposed above the guiding grooves to facilitate sliding passage of a support plate beneath the tapered tip.

7. Surgical apparatus according to claim 1 further including an support element having an aperture therein substantially aligned with the elongated body and being attached within the arched shape near the proximal end of the body for supporting an endoscope within the aperture.

* * * * *